United States Patent [19]
Shapira

[11] Patent Number: 5,290,605
[45] Date of Patent: Mar. 1, 1994

[54] SUN-EXPOSURE NUTRITIONAL SUPPORTING COMPOSITION

[76] Inventor: Niva Shapira, 5 K Zitomir, Tel-Aviv, Israel

[21] Appl. No.: 962,058

[22] Filed: Oct. 16, 1992

Related U.S. Application Data

[63] Continuation of Ser. No. 545,071, Jun. 28, 1990, abandoned.

[30] Foreign Application Priority Data

Jun. 29, 1989 [IL] Israel ................................. 090794

[51] Int. Cl.⁵ ............................................. A61K 47/00
[52] U.S. Cl. .................................... 424/439; 424/401
[58] Field of Search ................ 424/401, 439; 514/904, 514/775, 725; 426/590, 524

[56] References Cited

U.S. PATENT DOCUMENTS

| | | | |
|---|---|---|---|
| 2,300,410 | 11/1942 | Ferrari | 514/775 |
| 2,694,668 | 11/1954 | Fricke | 514/904 |
| 2,980,588 | 5/1961 | Larde | 514/904 |
| 3,036,957 | 5/1962 | Lehman | 514/904 |
| 3,920,834 | 11/1975 | Klaui et al. | 514/547 |
| 4,599,234 | 7/1986 | Amer | 514/725 |
| 4,690,820 | 9/1987 | Simko | 514/904 |
| 4,808,428 | 2/1989 | Forsstrom | 426/590 |
| 4,876,106 | 10/1989 | Sabatura | 426/590 |
| 4,921,877 | 5/1990 | Cashmere | 514/904 |
| 4,929,774 | 5/1990 | Fukamachi | 568/825 |

OTHER PUBLICATIONS

American Hospital Formulary Drug Information; 1989 Ed., Pub. by Am. Soc. Hosp. Pharmacists, pp. 2036-2037.
Am. J. Clin Nutr 1987; 45: 1368-77, Gey et al., Plasma Levels of Antioxidants vitamins.
Drug Facts and Comparisons, 44th Ed., Lippincott Company, pp. 6-7.
Santamaria et al.; Living in a Chemical World, vol. 534, 1988, "Chemoprevention of Indirect and Direct Chemical . . ." pp. 584-596.
Bendich et al.; The FASEB Journal; vol. 3, Jun. 1989; "Biological actions of carotenoids" pp. 1927-1932.
Deleo; "Prevention of Skin Cancer" Dermotol. Surg. Oncol vol. 14:8; Aug. 1988; pp. 902-906.

Primary Examiner—Thurman K. Page
Assistant Examiner—William E. Benston, Jr.
Attorney, Agent, or Firm—Jacobson, Price, Holman & Stern

[57] ABSTRACT

A nutritional soft drink for protection against the danger of exposure to UV light. The drink comprises a mixture of carotenoids, optionally together with vitamin C and/or vitamin E and/or other physiologically acceptable antioxidants in an amount which does not exceed 10 vitamin ARDA equivalents of provitamin A per liter of drink. Other biologically acceptable flavors and/or additives may be added. The drink may be in liquid drinkable form or in frozen or semi-frozen form.

13 Claims, No Drawings

SUN-EXPOSURE NUTRITIONAL SUPPORTING COMPOSITION

This application is a continuation of application Ser. No. 07/545,071, filed Jun. 28, 1990 now abandoned.

The present invention relates to a nutritional soft drink containing carotenoids, which are useful as protecting agents against damages due to exposure to UV light, particularly skin cancer in humans.

It has been known for a long time that UV light is a major cause of skin cancer. The art employs numerous protecting agents against the dangers of exposure to UV light, particularly protective materials to be applied topically to the skin, such as sun ointments and lotions, be they water, alcohol or oil based, which contain photo-protectant materials. This approach—so far the only effective approach widely used and accepted—has the considerable drawback of requiring high amounts of active photo-protectant materials, some of which have recently become suspect of becoming toxic under these conditions and in different ways harmful to health. Furthermore, obtaining a constant and uniform coverage of the skin with protecting ointments is difficult, and also the effectiveness of such protectants to defend the skin against UVA radiation is debatable.

Systemic carotenoids and antioxidants, both with and without Pro-Vitamin A activity, have been known for some time to be effective as protective agents against sun exposure hazards.

Recently, it has been suggested to increase carotenoids consumption by dietary modification or oral administration of carotenoid supplements, e.g., gelatin capsules and/or tablets. The said approach does not provide an optimal regime because appetite is decreased by exposure to sun and heat, and because intake of antioxidants in concentrated form, e.g., by swallowing tablets which should preferably be taken with meals, may expose to uneven dosages of antioxidants which may be associated with metabolic interference and even toxicity.

Such systemic approaches, furthermore, have the considerable drawback of being unsynchronized with the actual exposure to sunlight and therefore unnecessarily high—or ineffectively low—amounts of protective agents can be found in the system.

It is therefore clear that it would be highly desirable to provide a vehicle through which intake of carotenoids and other systemic photo-protectants can be applied in a proportional manner, without substantially exceeding the amount which is necessary for achieving substantial physiological protection from exposure to sun radiation, and/or exceeding the RDA generally accepted safe limitations.

It is an object of the present invention to provide a sun-exposure nutritional supporting drink which contains carotenoids as the basic photo-protectants, which overcomes the drawbacks of the methods known in the art and which provides compensatory increased levels of photo-protectants and antioxidants in the body when most needed, because they are quickly consumed or otherwise their concentration in the system decreases at a high rate, thus affording a systemic protective action.

The invention is therefore directed to a soft drink which contains a carotenoid mix, alone or together with vitamin C and/or vitamin E and/or other antioxidants, in an amount which does not exceed 10 Vitamin A RDA (Recommended Daily Allowance) equivalents of pro-Vitamin A carotenoids per liter of cool drink. Thus, intake of carotenoids and related photo-protectants is a function of exposure to sun and heat. The more exposed is the subject to the sun, the greater the amount of carotenoids that he will consume, because thirst and drinking responses are evoked proportionally to the extent/level of exposure to sun and heat.

It should be understood that the addition of Vitamins C and E or selenium to the carotenoids-containing drink has a synergistic effect, inasmuch as reduced glutathione (GSH) and Vitamin E are involved in the prevention of peroxidation of nuclear material, and Vitamin C, through its regenerating effect on Vitamin E is also active in this fashion. Thus, these additives can contribute protection in the initiation phase of skin damage, whereas carotenoids are rather effective in the later promotion stages of the photo-process.

Additional useful additives comprise antioxidants and factors directly or indirectly related to radical scavengers, such as GSH or Se, and CoQ10. These may be added as isolated materials or as naturally occurring components of vegetable/fruit juices and/or herbal preparations.

Normally a carotenoids mix will contain a number of carotenoids, such as $\beta$-carotene, canthaxanthin, zeaxanthin, lycopen, lutein, crocetin, capsanthin, etc. The RDA equivalent of such a mix will be calculated based on the relative pro-Vitamin A activity of the carotenoids which do have pro-vitamin activity, e.g., $\beta$: 100%, $\alpha$: 50-54%, $\gamma$: 42-50%, $\beta$-zeacarotene: 20-40%, cryptoxanthin: 50-60%, $\beta$-apo-8'-carotenal: 72%, $\beta$-apo-12'-carotenal: 120%, etc., assuming that all the carotenoids with provitamin activity will be converted into Vitamin A.

Among the various advantages of the invention, it should be mentioned also that a drink is an excellent vehicle for the purposes of the invention, because it is generally accepted and proven that drinking in warm weather is beneficial. Furthermore, thirst can be induced by the addition of sugars or equivalent materials in relatively high proportions, to stimulate further drinking. Stimulation of the will to drink the mix according to the invention will be better achieved, of course, with tasty drinks.

Using the drink of the invention as the application method, the danger of overdosage becomes minimized, because overdosage may occur whenever a too-high amount of material is absorbed, which is not subsequently utilized by the body because it is not highly needed by the body as when exposed to sun in a manner that will prime the body to consume the photo-protectants. With the proportional intake of material through the drink according to the invention, this problem is inherently resolved.

It has further been found that Vitamin C protects carotenoids and, therefore, the addition of Vitamin C permits to operate with lower carotene concentrations, which is of course desirable. Furthermore, synergism between Vitamin C and Vitamin E exists, inasmuch as Vitamin E (tocopherol) is regenerated from tocopheryl radical by Vitamin C.

Vitamin C can also be supplied in other forms or precursors which can be metabolised to obtain Vitamin C, such as ascorbyl palmitate. Ascorbyl palmitate itself was found more effectively protecting carotene and internal organs, e.g., liver, against free radicals, when compared to ascorbic acid. This might be because it is easier to dissolve in fatty tissues.

While the limiting amount of pro-Vitamin A carotenoids and vitamins to be taken daily are of course the updated RDA, some examples of increased concentrations and other compositions to be used according to the invention will be detailed hereinafter. It is of course understood that the following examples are provided only for the purpose of illustration, and have no limiting purpose. Various flavors and additives detailed hereinafter are also detailed only by way of example, and a person skilled in the art will be able to provide additives, flavors and the like which match the drink which it is desired to provide.

Among the many additives which can be employed, tonic herbs are possible convenient additives, including, e.g., Borrage, Aloe-Vera, Peppermint, Lemon, Ginseng, Barley-water, Anise, Grapes, Raspberries, Strawberries, Hawthorn berries, Rosemary, Watercress, Guarana, Papavera Rhoea, Achilea Milfolia, Arcitium Lappaa, Chrysanthemum, Parthenium, Cola vera, Elentherococcus, Bingo Bilboa, Japanese apricot (UMA) etc.

The following examples of compositions will illustrate some of the many possible uses of the invention. While some examples of active material contents are specified hereinafter, the man of the art will appreciate that many different combinations of carotenoids and other active ingredients can be provided, depending on the requirements from the final composition concerning flavor, color, RDA, etc.

In general, addition of active materials can be done, e.g., by following the general directions given below.

Milk/Fat Soluble Liquids

Fat emulsion carotenoid mix: $\beta$-carotene 30% suspension: 8 mg (for light drinks, e.g., Pina Colada) up to 25 mg (butter raspberry), 60 mg (cocoa), for each liter of cocoa/raspberry butter milk preparation. Apocarotenal (yellow-orange brown color), 30% fat emulsion base: 5–15 mg/liter for cocoa, and other coffee-based liquids and ices. Canthaxanthin 1% water soluble: 500–2000 mg/liter in strawberries and cocoa preparations. $\alpha$-tocopherol (e.g., Hoffmann-La Roche): 0–400 mg/liter drink.

Water-Based Drinks

Carotenoid mix such as canthaxanthin 10% (water soluble) powder and $\beta$-carotene 1% powder. Dark drinks such as raspberries, strawberries or cola will contain (for each liter) the following: 350–2500 mg $\beta$-carotene 1%. and 500–1500 mg canthaxanthin 10%. Apo-carotene 30% fat emulsifier base, 1:1 mixed with emulsifier for ginger ale: 5–15 mg/liter.

For light colored drinks, mostly $\beta$-carotene, e.g., 350 mg/liter for lemon drink and 700–2500 mg/liter for mint drinks.

Vitamin C: water soluble mix: L-ascorbic acid or ascorbate salts, according to taste considerations, between 50–2000 mg/liter. Ascorbyl palmitate (water insoluble) mix: 1:1 ratio or ascorbyl palmitate and emulsifier: range of use: 200–8000 mg mix/liter drink.

EXAMPLE 1

Instant Mandarin-Orange Powder

A powder to be dissolved in water (130 g/liter) is prepared by admixing the following ingredients: 82.73% sucrose/white sugar, 10% flavorings (such as HNR flavor mandarin-orange 48230), 3% citric acid, 3% dextrose, 1% cloudifier (e.g., HNR). Buffers: 0.5% tri-sodium citrate, 0.5% tri-calcium phosphate. 0.2% ascorbic acid, 0.07% food color.

Diet version: Based on a sweetness index of sucrose=1, 1/200 parts of Aspartane or 1/250 parts of Acesulfame-K are substituted for each part of sugar.

To the above there are added 1–5 RDA equivalents of $\beta$-carotene and $\alpha$-tocopherol in water base emulsion and L-ascorbic acid (Hoffmann-La Roche) or ascorbyl palmitate (ICN Biochemicals).

EXAMPLE 2

Orange Drink

An orange drink can be prepared containing 150 g juice (10.5 BX) or 24.6 orange concentrate 64 BX, 89.25 g sucrose, 2.77 g lemon acid, flavors, stabilizers, buffer citrate (to prevent tartar) and extracts, 883.38 g water, carotenoids mix: 8 mg %, Vitamin C equivalent: 20 mg %.

The composition of the invention can also be provided in a milk/fat-water emulsion. The following are examples of such compositions.

EXAMPLE 3

Instant Chocolate Beverage

A formulation (8–10%/liter milk) will contain 67% sucrose/sugar, 30% cocoa powder, 1% lecithine and 2% satia gum, carotenoid mix, 6 mg %, Vitamin E, E.E. ($\alpha$-tocopherol equivalent) 6 mg %, coenzyme Q10.

EXAMPLE 4

Vegetarian Milk Base: Pinacolada

The drink will contain 5% coconut oil, 0.1% emulsifiers, 8–10% sugar, 0.1% pinacolada flavor, and active ingredients as in the previous examples.

EXAMPLE 5

Ice Cream

An ice cream may contain about 10% of fat, 12% fat-free milk solids, 15% sugar, 3% corn syrup, color extracts and flavors, and active ingredients as in the previous examples.

EXAMPLE 6

Raspberry Ice Butter-milk

Butter-milk 61.45%, raspberry pulp 15.5%, sucrose 14%, corn syrup 6%, butter 3%, emulsifier (lecithine) 0.2%, stabilizers e.g., Lygomme ELB 0.2% (pH 3.8–4.0), active ingredients as in the previous examples.

EXAMPLE 7

Camomille Summer Punch (Tonic)

A strong infusion (concentrated hot-water herbal extract with or without ¼ ethanol) with pineapple, papaya and honey. Add mint and strawberry cubes for color and taste. Active ingredients as defined above.

EXAMPLE 8

Herbal (Mint) Drops

A strong infusion: 4–8 teaspoons peppermint in 1 cup boiling water, steeping the infusion in a covered container for a few hours, refrigerated. 50 Drops added to lemonade drink. Active ingredients as defined above.

EXAMPLE 9

Teas

Rose Hip Tea Blend (cold Vitamin C drink):

1 cup dried rose hips, 1 3-inch stich cinnamon, ¼ cup dried lemon balm leaves, 1 teaspoon dried grated organic lemon rind.

Rose Hip and Blackberry Cordial:

2 teabags rose hips (Pompadour brand), 1-2 teaspoons blackberry cordial, 1 cup boiling water. Steep together and serve.

Peppermint-Alfalfa Tea Blend:

1 cup peppermint or spearmint or bee balm leaves, 1 cup dried alfalfa leaves.

Active materials as defined above.

EXAMPLE 10

Lemon Mint Blend

Water Preparation

½ cup dried peppermint leaves, 1 cup dried alfalfa leaves, 3 tablespoons dried lemon balm leaves, 3 tablespoons dried, grated lemon rind. Solids: 1 teaspoon (250 g sucrose/liter). Active ingredients as defined above.

EXAMPLE 11

Compound Barley Water 2 pints simple barley water (4 ounces barley, whole, 2 ounces honey, lemon peel washed of ½ lemon: Add 1 pint of water to barley and lemon peel. Simmer until soft. Remove from heat. Steep. Add honey.), 1 pint hot water, 2½ ounces sliced figs, ½ ounce, sliced and bruised licorice root, 2½ ounces raisins. Boil down to 2 pints. Strain.

EXAMPLE 12

Ginger Ale 1 large piece ginger root, bruised, 1 pint boiling water, 1 tablespoon honey, Perrier water as needed. Boil water, add bruised ginger root and simmer for fifteen to twenty minutes. Strain out root. Add honey and mix well. Combine with Perrier water. Don't use powdered ginger.

EXAMPLE 13

Drink Powder

"Orange Taste"

(values expressed as percentage/content in the end user preparation): 10% sugar, 1% carotene mix. (Diet should be 1/200 aspartame or 1/250 acesulfam.) 0.1% citric acid. 0.9% tasters. 0.1-0.2% stabilizers (CMC, guargum, etc.). Buffer—$Na_3$ citrate extracts.

As will be apparent from the above examples, preparing a mixed carotenoids drink according to the invention is simple and economic. It should be understood, as detailed above, that the word "drink" throughout this specification is meant to include also frozen or semi-frozen liquids, such as ice cream and sorbets.

EXAMPLE 14

Fruit Ice Strawberry Sorbet

Sucrose 21.5%, corn syrup (DE 36-38) 6.5%, strawberry puree 24.15%, strawberry concentrate 2.5%, satia algin GAX-900 0.35%. pH 3.3-3.5, water 45%.

Weed juice and pineapple: mint, alfalfa, filaree, dandelion, romaine leaves, parsley, celery tops, carrot tops, 2 cups pineapple: Combine handfuls and extract into juice. Place handfuls of these weeds and home greens in the juice extractor, use 1 cup to each 2 cups of pineapple. This green juice may be made into ice cubes and used.

Nutritional and RDA data for the components of the drink of the invention are well known to persons skilled in the art, and change from time to time. Illustrative data are reported below, based on values accepted at the time of filing of this application:

RDA was formerly defined in terms of International Units, I.U., defined as 0.3 μg of crystalline all-trans retinol, or 0.6 μg β-carotene. Since 1980, RDA for Vitamin A is commonly stated in μg and R.E. For the adult male, the RDA is set at 1000 RE (750 as retinol and 250 as β-carotene, 5000 I.U.), while the RDA for women is lower, at 800 RE (4000 I.U.). Children need 400 to 1000 RE (2000 to 5000 I.U.), increasing from infancy to 14 years. The amount of β-carotene required for 1 RE is 6 μg, while the amount required for other provitamin A carotenoids is 12 μg. 1 RDA carotene is the provitamin A equivalent of 5000 I.U. Vitamin A.

I claim:

1. A synergistic food-stuff composition concentrate consisting essentially of
    (A) one or more edible carotenoids selected from the group consisting of α, β and γ carotenes, zeaxanthin, lycopen, lutein, crocetin, capsanthin, β-zeacarotene, cryptoxanthin, β-apo-8'-carotenal and β-apo-12'-carotenal;
    (B) water;
    (C)(1) at least one physiologically-acceptable antioxidant selected from the group consisting of ascorbic acid and salts thereof, and tocopherols; or
    (2) at least one physiologically-acceptable free-radical scavenger selected from the group consisting of reduced glutathione and coenzyme Q10; or
    (3) at least one physiologically-acceptable antioxidant selected from the group consisting of ascorbic acid and salts thereof, and tocopherols, and at least one physiologically-acceptable free-radical scavenger selected from the group consisting of reduced glutathione and coenzyme Q10.

2. A food-stuff composition for oral consumption comprising an effective amount of the concentrate according to claim 1 for systemic protection against the harmful effects of solar radiation, wherein the concentration of component (A) of the concentrate in said food-stuff composition does not exceed 10 times the U.S. recommended daily allowance for provitamin A active carotenoids per liter.

3. A method for protecting against the harmful effects of exposure to solar radiation, comprising orally administering to a person in need of such protection during exposure to solar radiation a prophylactic effective amount of a synergistic food-stuff composition comprising:
    (A) at least one edible carotenoid selected from the group consisting of α, β and γ carotenes, zeaxanthin, lycopen, lutein, crocetin, capsanthin, β-zeacarotene, cryptoxanthin, β-apo-8'-carotenal and β-apo-12'-carotenal;
    (B) water;
    (C) (1) at least one physiologically-acceptable antioxidant selected from the group consisting of ascorbic acid and salts thereof, and tocopherols; or (2) at least one physiologically-acceptable free-radical scavenger selected from the group consisting of reduced glutathione and coenzyme Q10; or (3) at least one physiologically-acceptable antioxidant selected from the group consisting of ascorbic acid and salts thereof, and tocopherols, and at least one physiologically-acceptable free-radical scavenger selected from the group consisting of reduced glutathione and coenzyme Q10;

wherein when the composition is administered the amount of carotenoids does not exceed 10 times the U.S. recommended daily allowance for provitamin A active carotenoids per liter.

4. The composition of claim 2, further comprising a flavoring selected from the group consisting of borrage, aloe-vera, peppermint, lemon, ginseng, barley-water, anise, grapes, raspberries, strawberries, hawthorn berries, rosemary watercress, guarana, papavera rhoea, achillea milfolia, arcitium lappa, chrysanthemum, cola vera, eleutherococcus, ginkgo biloba and japanese apricot.

5. The composition of claim 2, wherein the antioxidant is ascorbic acid or a salt thereof.

6. The composition of claim 2 wherein the antioxidant is a tocopherol.

7. The composition of claim 1, wherein the antioxidant is an alpha tocopherol.

8. The composition of claim 2, wherein the composition is in an emulsified base.

9. The composition of claim 2, wherein the composition is in a milk base.

10. The composition of claim 2, wherein the composition is in a concentrated form.

11. The composition of claim 2, wherein the composition is in a drinkable form.

12. The composition of claim 2, wherein the composition is in a semi-frozen form.

13. The composition of claim 2, wherein the composition is in a frozen form.

* * * * *